United States Patent

Ikeda et al.

Patent Number: 6,051,392
Date of Patent: Apr. 18, 2000

[54] METHOD FOR QUANTITATING A SUBSTRATE AND MEASUREMENT DEVICE USED THEREFOR

[75] Inventors: Shin Ikeda, Katano; Motokazu Watanabe, Kadoma; Toshihiko Yoshioka; Shiro Nankai, both of Hirakata, all of Japan

[73] Assignee: Matsushita Electric Industrial Co., Ltd., Osaka-fu, Japan

[21] Appl. No.: 09/328,510

[22] Filed: Jun. 9, 1999

[30] Foreign Application Priority Data

Jun. 10, 1998 [JP] Japan .................. 10-162411

[51] Int. Cl.[7] .................. C12Q 1/26; C12Q 1/54
[52] U.S. Cl. .................. 435/25; 435/283.1; 435/14; 435/817
[58] Field of Search .................. 435/25, 283.1, 435/14, 817

[56] References Cited

U.S. PATENT DOCUMENTS 4,711,245  12/1987  Higgins et al. .................. 435/283.1

FOREIGN PATENT DOCUMENTS 03202764  4/1991  Japan .

*Primary Examiner*—Louise N. Leary
*Attorney, Agent, or Firm*—McDermott, Will & Emery

[57] ABSTRACT

The present invention provides a measurement device facilitating accurate quantitation of a substrate from a trace amount of sample and a highly reliable quantitating method of a substrate. The method uses an analysis element comprising a pair of electrodes for electrochemically quantitating reaction between a substrate in a sample and an oxidoreductase. One of the electrodes of the analysis element is a membrane formed on an inner wall of a cylindrical hollow space having an opening and the other is a needle. The needle electrode is projected temporarily external to the hollow space to puncture a subject and the resultant sample is collected from the subject.

6 Claims, 6 Drawing Sheets

METHOD FOR QUANTITATING A SUBSTRATE AND MEASUREMENT DEVICE USED THEREFOR

BACKGROUND OF THE INVENTION

The present invention relates to a method for quantitative measurement of a substrate such as sucrose, glucose, etc. contained in a sample based on enzyme reaction, and to an analysis element used therefor.

Currently, there is an increasing demand for a method that facilitates simplified quantitative analysis of blood sugar and urine sugar levels at home.

Conventionally developed methods for quantitating sugars such as sucrose, glucose, etc. use polarimetry, colorimetry, reduction titration and a variety of chromatography. All the prior methods, however, have a drawback that their application at home with ease is difficult. For example, the method using polarimetry permits simplified manipulation but is greatly affected by the temperature at measurement. This method has another drawback of being difficult to make accurate measurement of blood polarization with a simple instrument. Moreover, all the above-mentioned conventional methods have only poor accuracy due to their lower specificity to sugars.

Under the circumstance, a biosensor that utilizes specific catalytic action of enzyme has been developed in order to facilitate simplified quantitation of sugar level at home.

In the following, a method for quantitating glucose will be described as one example of the method for quantitative measurement of sugar level using a biosensor.

A commonly known method for electrochemically quantitating glucose is a method which combines glucose oxidase (EC1.1.3.4; hereinafter abbreviated to "GOD") as an enzyme with an oxygen electrode or hydrogen peroxide electrode (for example, "Biosensor", edit by Shuichi Suzuki, published by Kodansha).

GOD can selectively oxidize a substrate β-D-glucose to D-glucono-δ-lactone in the presence of an electron acceptor. If present, oxygen can function as an electron acceptor and is reduced to hydrogen peroxide by GOD-mediated oxidation reaction. This means that the decreased amount of oxygen or increased amount of hydrogen peroxide is proportional to the content of glucose in a sample. Therefore, glucose concentration in a sample can be quantitated by reacting a glucose containing sample with an enzyme in the presence of oxygen and measuring the resultant decrease in oxygen amount using the oxygen electrode or the resultant increase in hydrogen peroxide amount using the hydrogen peroxide electrode.

However, as speculated from the reaction of the above method, quantitation using a biosensor as shown above is largely affected by the oxygen concentration in the sample. Moreover, absence of oxygen in a sample solution disables the measurement.

Therefore, there is a proposed new type of glucose sensor that uses an organic compound or a metal complex, such as potassium ferricyanide, ferrocene derivatives, quinone derivatives or the like, as the electron acceptor in place of conventional oxygen. Measurement method using such new sensor oxidizes reduced form electron acceptors resulting from enzyme reaction on one electrode of the sensor in order to determine the substrate concentration, such as glucose, in the sample based on the resultant oxidation current. The use of such organic compound or metal complex as the electron acceptor enables to form a reaction layer including a known amount of GOD and electron acceptor while securing their precise and stable existence on the electrodes. Further, it enables to integrate the resultant reaction layer with the electrodes while securing an almost dry state of the reaction layer. Disposable glucose sensors based on the above technology have been drawing much attention currently. One representative is a biosensor disclosed in the Japanese Patent No. 2517153. This disposable glucose sensor facilitates measurement of the glucose concentration in a sample solution by simple insertion of the sample solution into a sensor detachably connected to a measurement device. Such measurement method is not limited to glucose quantitation and may be applicable to quantitation of other substrates in a sample.

Such prior biosensor as shown above can measure a substrate from a sample of several $\mu l$. However, there is a serious demand in various fields of art recently for the development of an analysis element that facilitates measurement of a substrate from a trace amount of sample, i.e., less than 1 $\mu l$. No technology, however, has so far been successful in decreasing the amount of sample drastically. Conventional measurement of, for example, sugar level has been as follows: Primarily, blood is leaked on the skin surface by puncture using a puncture-specific instrument, such as lancet, and then the blood sample-is introduced into a sensor mounted on a measurement-specific device for quantitation of blood sugar level. The use of a trace amount of sample can worsen measurement accuracy because the sample is dried before measurement. For a maximal decrease of the effect of drying on the measurement, the interval between blood sampling and sample introduction into the sensor must be shortened. The above method, however, has a limitation in shortening the interval because it necessitates individual sampling-specific and measurement-specific instruments as noted above.

Moreover, in normal conventional biosensors, a pair of electrodes are arranged on the same plane. Such structure is prone to produce inhomogeneous distribution in density of current flowing in an electrode upon voltage application onto the electrode, which can result in significant errors in measurement.

BRIEF SUMMARY OF THE INVENTION

The present invention solves the above-mentioned problems associated with the prior art and provides a method for quantitating a substrate that facilitates accurate quantitation of a substrate from a trace amount of sample.

A method for quantitating a substrate of the present invention uses an analysis element comprising: a needle electrode; a membrane electrode; and a cylinder having a hollow space, the hollow space being open at least one end thereof, wherein the needle electrode is accommodated in the hollow space and the membrane electrode is formed on an inner wall of the hollow space.

The method for quantitating a substrate of the present invention comprises the steps of:

pressing an open end of the cylinder against a subject to be examined;

projecting a tip of the needle electrode external to the open end of the cylinder temporarily to puncture the subject and collecting a sample such as body fluid from the subject;

introducing the collected sample between the membrane electrode and the needle electrode in the cylinder;

reacting a substrate contained in the sample with an oxidoreductase; and applying a voltage across the membrane electrode and the needle electrode and measuring resultant current in the membrane electrode or in the needle electrode.

A measurement device for the quantitating a substrate of the present invention, the needle electrode is accommodated in the hollow space of the cylinder in a manner such that the axis of the electrode is in the direction of the axis of the hollow space. This arrangement produces an opposed arrangement of the needle electrode to the membrane electrode and secures homogeneous current density upon application of a voltage across the two electrodes. This enables accurate detection of electrochemical reaction of the sample. At that time, narrowing of a gap between the needle electrode and the lumen of the hollow space helps the sample to penetrate throughout the hollow space by capillary phenomenon which facilitates measurement.

Another preferred mode of the measurement device of the present invention, the needle electrode is provided with an electrically insulating layer formed on a portion of the surface. A provision of the layer holds an area of the needle electrode constant and prevents short-circuiting between the needle electrode and the other electrode, that is, the membrane electrode formed on the inner wall of the hollow space.

It is preferable to form a reagent layer containing an oxidoreductase and an electron acceptor on the surface of the needle electrode or on the inner wall of the hollow space. A provision of the oxidoreductase and the electron acceptor close to an electrode system enables the analysis element to quantitate an analyte by simple supply of a sample thereto. More preferably, the reagent layer is formed directly on the surface of the electrode.

The measurement device in accordance with the present invention uses the analysis element having the above-mentioned structure and comprises a driving unit for moving the needle member of the analysis element such that its tip is projected external to one open end of the hollow space of the analysis element. At sampling body fluids, such as blood, from a body, while pressing an open end of the hollow space against the skin of the body, the tip of the needle electrode is projected external to the open end temporarily to puncture the skin. After puncture, the needle electrode is accommodated again in the hollow space. The body fluids leaking on the skin surface then penetrate throughout the hollow space by sticking to the needle electrode and via capillary phenomenon. In this way, the body fluids are supplied between the two electrodes and instantaneous measurement is enabled. At that time, since projection of the tip of the needle electrode can be momentary, the use of a spring for the driving unit is preferable from the aspect of cost and controllability.

Provision of a mechanism for fixing the needle electrode after the projection at the predetermined position makes it possible to maintain a distance between the electrodes and improves measurement accuracy.

As shown above, owing to the use of a three-dimensional arrangement of the electrode system, the present invention can reduce inhomogeneous distribution of current and therefore can provide a method for quantitating a substrate with high accuracy. According to the present invention, since sampling and substrate quantitation can be carried out rapidly, the amount of sample for measurement can be decreased.

While the novel features of the invention are set forth particularly in the appended claims, the invention, both as to organization and content, will be better understood and appreciated, along with other objects and features thereof, from the following detailed description taken in conjunction with the drawings.

It will be recognized that some or all of the Figures are schematic representations for purposes of illustration and do not necessarily depict the actual relative sizes or locations of the elements shown.

DETAILED DESCRIPTION OF THE INVENTION

In the following examples, the method for quantitating glucose will be described specifically as one representative method for quantitating a substrate, referring to the attached drawings.

First, an operation of the electrode system used in the present invention will be described.

Figure 1:
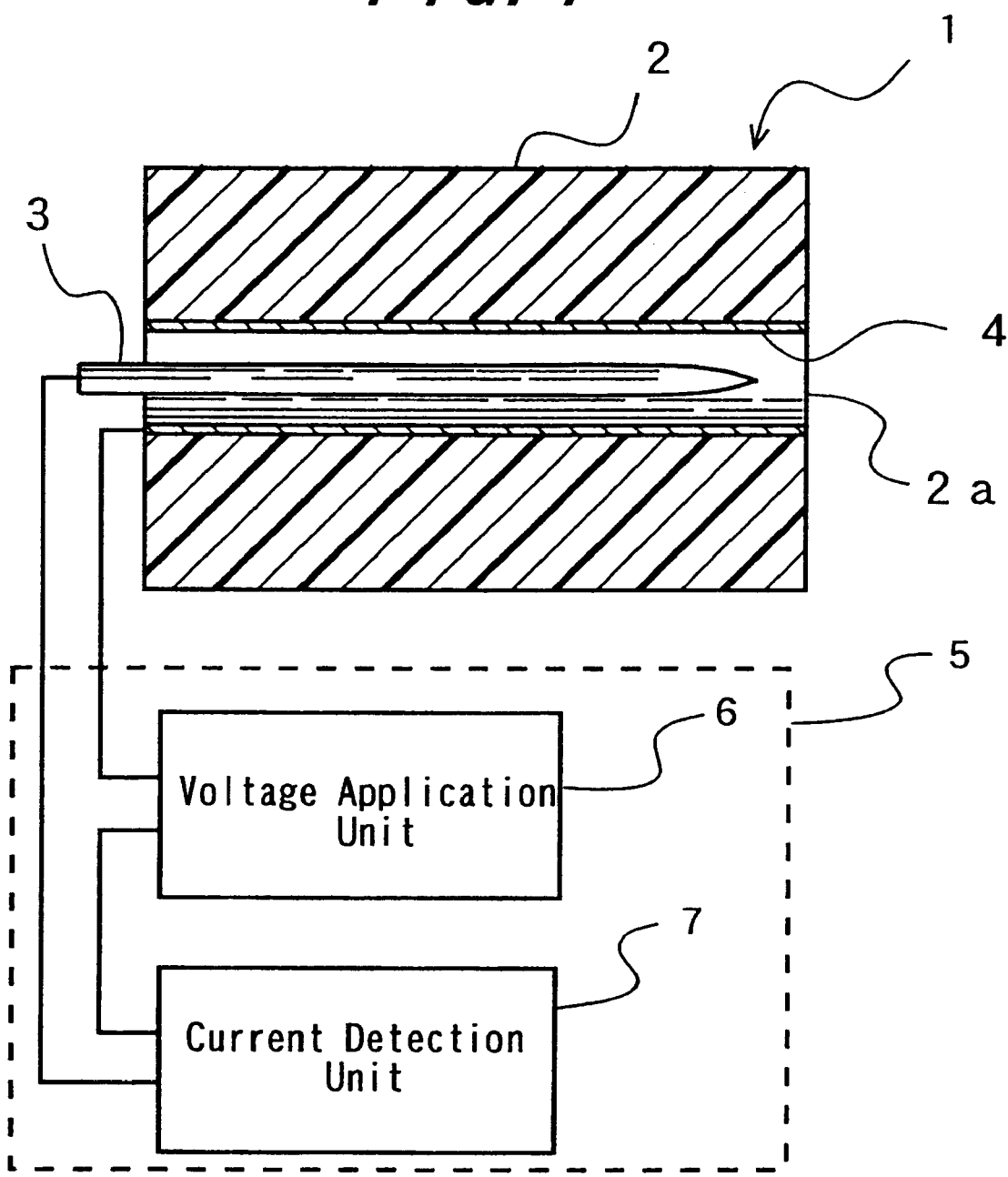
FIG. 1 is a sketch illustrating the structure of a measurement device of one example of the present invention.

FIG. 1 shows one example of the measurement device of the present invention. The measurement device is composed of an analysis element 1 and a main body 5.

The analysis element 1 comprises a cylindrical member 2 and a conductive needle member 3. The cylindrical member 2 which is made of a synthetic resin has a hollow space 2a with two open ends. The hollow space 2a is a cylinder measuring 1.2 mm in diameter and 10 mm in length. On a side wall of the hollow space 2a, a conductive membrane 4 mainly composed of silver is formed. The conductive membrane 4 can be formed, for example, by applying a paste containing a silver powder onto the side wall and drying it. The needle member 3 is mainly composed of carbon and measures 1.0 mm in diameter and 20 mm in length. The needle member 3 is arranged inside the hollow space 2a of the cylindrical member 2 such that the axis of the needle member is in the direction of the axis of the hollow space 2a. In the analysis element 1, the needle member 3 functions as a working electrode for detecting electrochemical reaction of a sample and the conductive membrane 4 functions as a counter electrode.

Both the needle member 3 and the conductive membrane 4 are connected to the main body 5. The main body 5 comprises a voltage application unit 6 for applying a constant voltage across the needle member 3 and the conductive membrane 4 of the analysis element 1 and a current detection unit 7 for detecting current flowing in the needle member 3.

The operation of the analysis element was confirmed by actual use of the measurement device.

A given amount of a solution containing GOD and potassium ferricyanide was mixed with several solutions with different concentrations of β-D glucose to formulate sample solutions with different β-D glucose concentrations. Each of the resultant sample solutions was stood still for a given time and introduced into the device through an opening of the hollow space 2a.

After introduction, the sample solution was penetrated throughout inside the hollow space by the capillary phenomenon and supplied between the needle member 3 and the conductive membrane 4.

Then, a voltage of 500 mV was applied onto the needle member 3 taking the conductive membrane 4 as reference and the resultant current flowing in the needle member 3 was measured. The result showed a current response proportional to the glucose concentration of the sample solution.

As evident from the above, measurement of oxidation current using the analysis element 1 enables measurement of glucose concentration in a sample. Since this particular analysis element of the present invention allows opposed arrangement of the working electrode (i.e., needle member 3) to the counter electrode (i.e., conductive membrane 4), current density on the electrode surface can be more homogeneous than that of other analysis element which arranges the two electrodes on the same plane. Therefore, the analysis element of the present invention enables substrate quantitation of higher accuracy.

The oxidation current as shown above results from an electrochemical reaction as follows.

In the presence of GOD, reactions of ferricyanide ions and glucose in the sample will take place which results in oxidation of glucose to glucono-lactone and reduction of ferricyanide ions to ferrocyanide ions. The concentration of the ferrocyanide ions is proportional to the glucose concentration. After enzyme reaction, when a voltage is applied to the sample, the ferrocyanide ions are oxidized to the original ferricyanide ions.

In this experiment, such oxidation current was measured by the needle member 3 of the analysis element 1.

As noted above, the use of an electrode system including a membrane electrode formed on the inner wall of the cylindrical member and a needle electrode accommodated inside the cylindrical member facilitates accurate and precise quantitation of a substrate.

In the following, concrete examples of a measurement device of a substrate comprising an identical electrode system and a function to directly sample body fluids from a body will be described.

EXAMPLE 1

Figure 2:
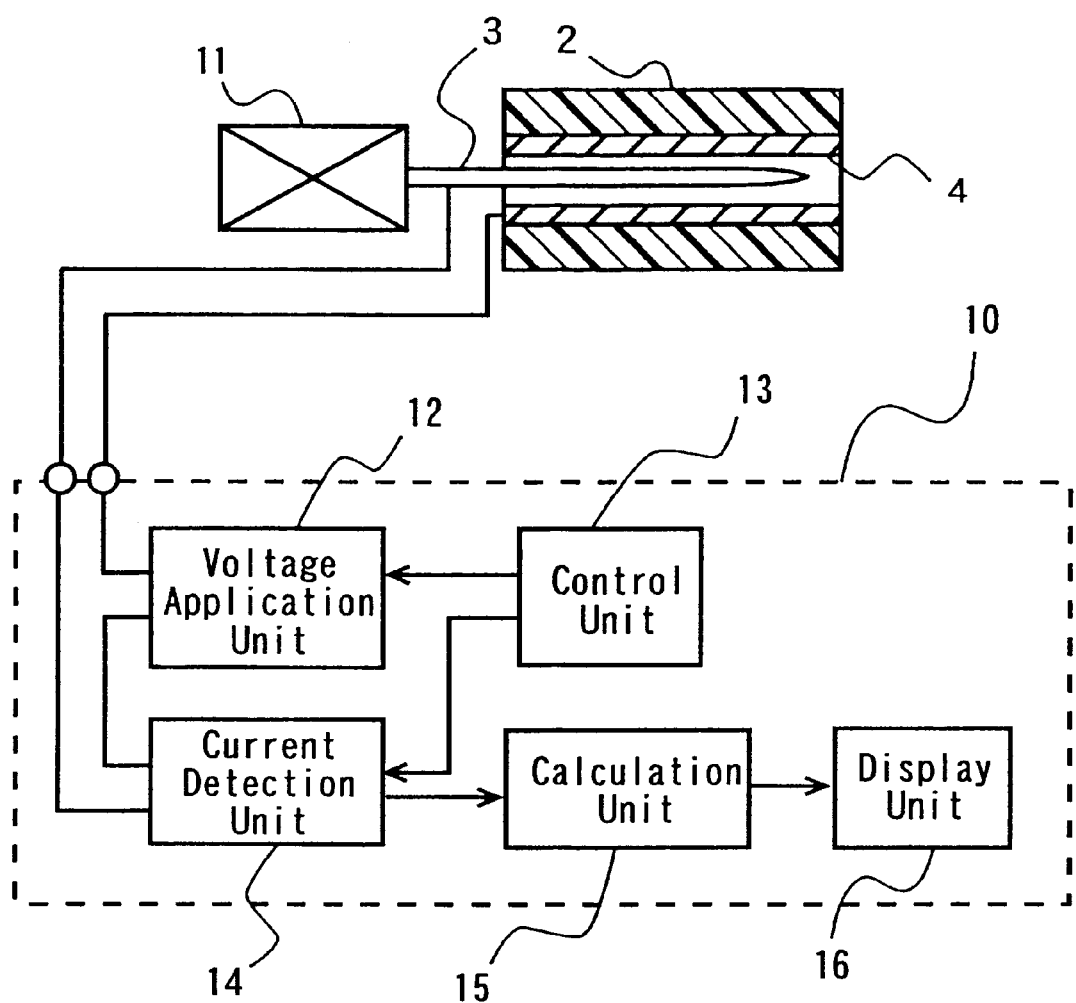
FIG. 2 is a sketch illustrating the structure of a measurement device of another example of the present invention.

FIG. 2 is a sketch showing the structure of the measurement device of this example. The device uses an analysis element comprising a needle member 3 and a cylindrical member 2 housing a membrane electrode 4. The device further comprises a driving unit 11 for projecting the needle member 3 external to an opening of the cylindrical member 2. The needle member 3 has another function as a puncture instrument.

An analyzer 10 of the device comprises a voltage application unit 12 for applying a voltage across the two electrodes of the analysis element, a current detection unit 14 for detecting current flowing in the electrode, a control unit 13 for controlling the voltage application 12 and the current detection 14 units, a calculation unit 15 for calculating a substrate concentration by comparing a current value detected by the current detection unit 14 with a current in response to standard substrate concentration which was stored in the calculation unit in advance, that is, a calibration curve, and a display unit 16 for displaying a calculated value by the calculation unit 15.

The control unit 13 senses a puncture by the needle member 3 and outputs a command signal to the voltage application unit 12 to apply a constant voltage of, for example, 500 mV onto the needle member 3 using the conductive membrane 4 as reference after a lapse of a given time (30 sec, for example). The current detection unit 14 detects current flowing in the needle member 3 upon voltage application, that is, oxidation current of the electron acceptor, based on a command signal output from the control unit 13.

Figure 3:
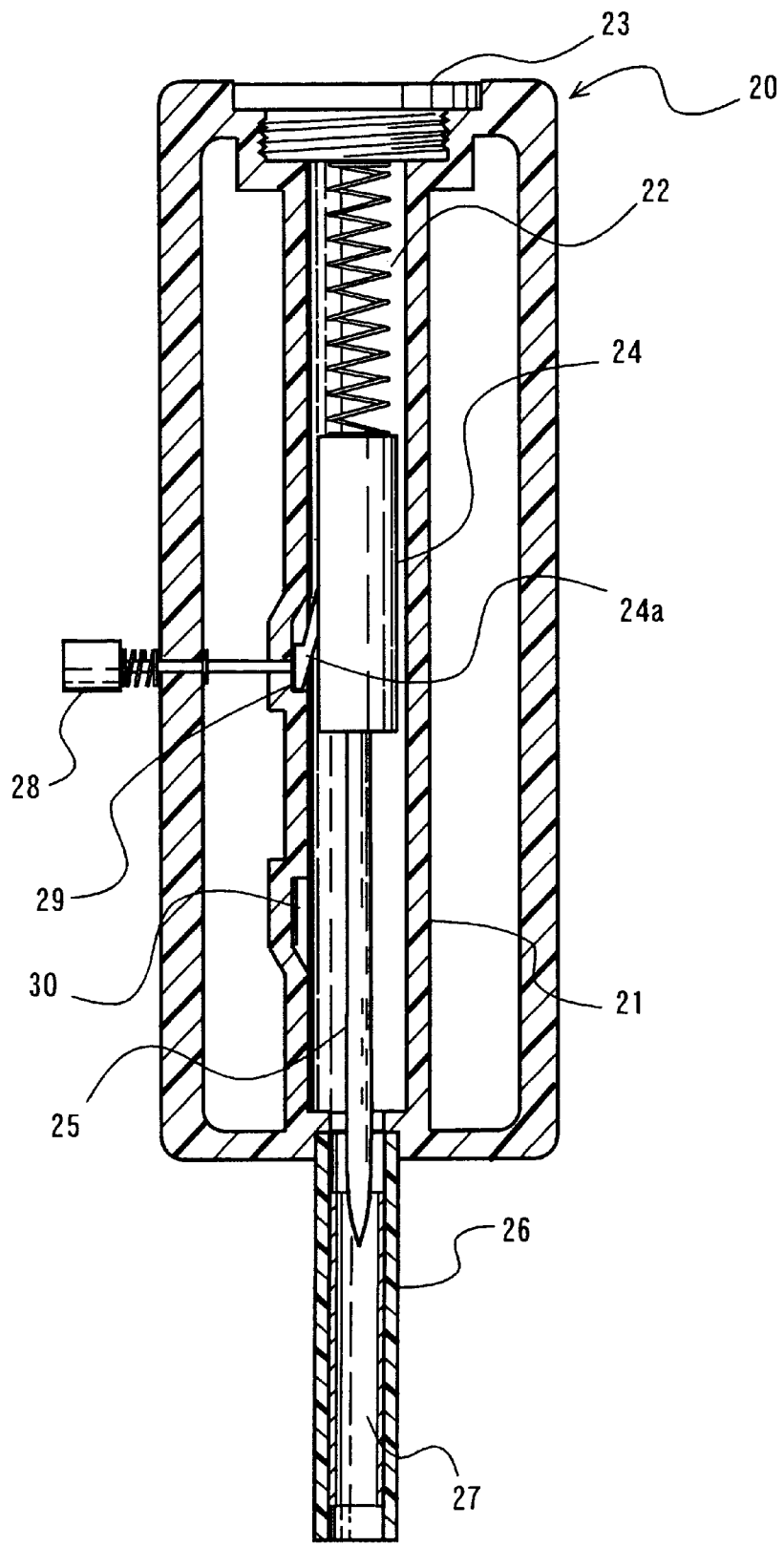
FIG. 3 illustrates a longitudinal cross-sectional view of the measurement device of the same example.

FIG. 3 shows one concrete example of the measurement device. A main body 20 is an integration of the above-mentioned driving unit and the analyzer.

A cylinder 21 of the main body 20 accommodates a cylindrical needle holder 24 shaped approximately in correspondence with the shape of an inner wall of the cylinder 21. The cylinder 21 has a cap 23 being screwed into one end thereof. The cylinder 21 has a cylindrical member 26 detachably fitted at the other end thereof.

The cylindrical member 26 is formed with a conductive membrane 27 as a counter electrode on an inner wall thereof similar to that in FIG. 2. The conductive membrane 27 has a reagent layer containing GOD and potassium ferricyanide formed on the surface thereof (not shown).

The needle holder 24 is connected to the cap 23 via a spring 22. At a tip of the needle holder 24, a needle 25 mainly composed of carbon is mounted. The needle 25 Jd should be detached after unscrewing the cap 23 from the main body 20 and taking out the needle holder 24. The needle 25 doubles as a working electrode.

Before measurement, the needle holder 24 is secured to a step 29 formed on the inner wall of the cylinder 21 via a stopper 24a as shown in FIG. 3. At this stage, the spring 22 is compressed.

Figures 4A, 4B:
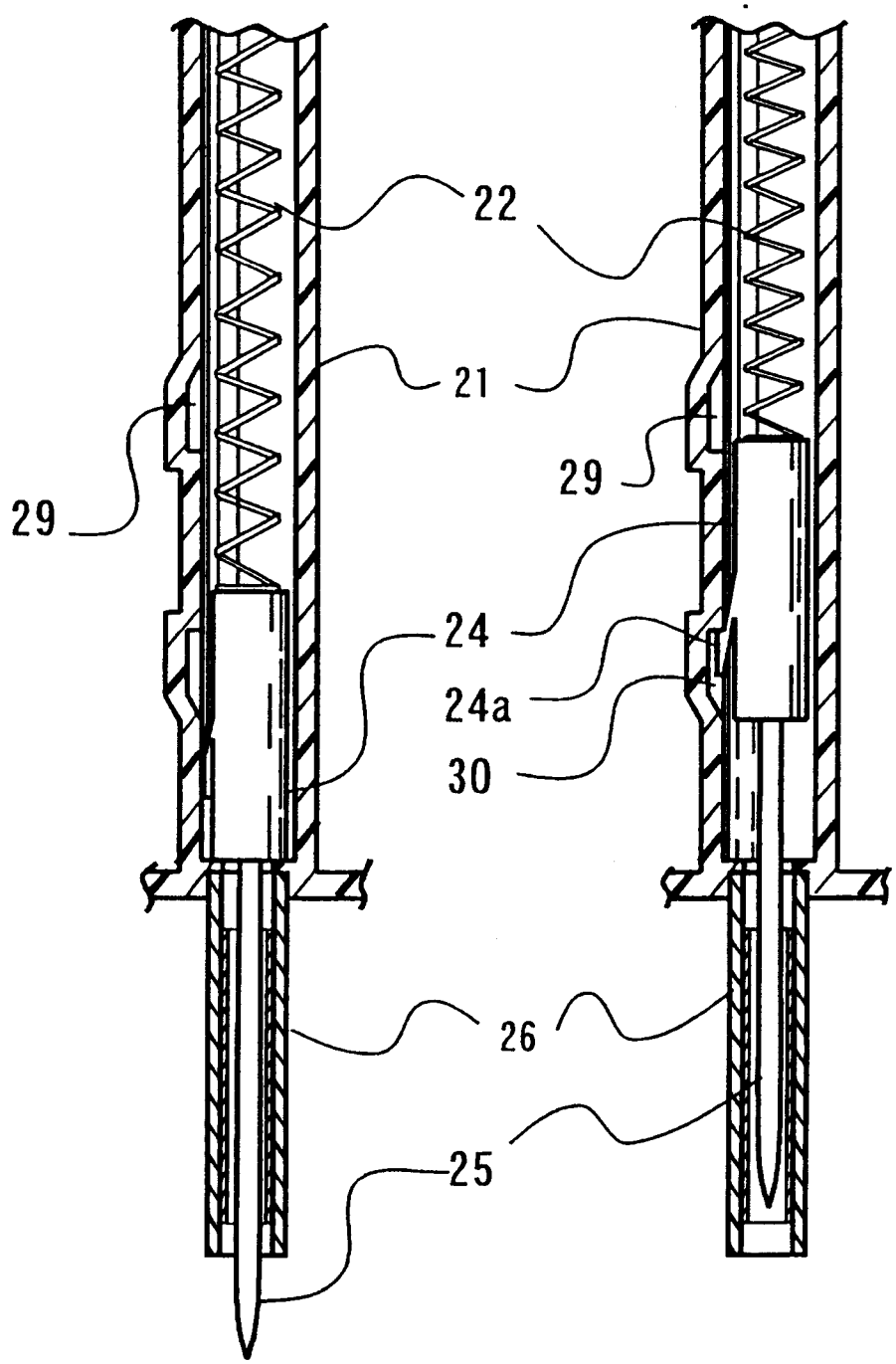
FIG. 4a illustrates a longitudinal cross-sectional view of the same measurement device at puncture of the skin.
FIG. 4b illustrates a longitudinal cross-sectional view of the same measurement device at measurement.

A user presses an opening of the cylindrical member 26 against the skin of a subject to be examined and pushes a switch 28. As a result, the stopper 24a is released from the step 29 and the needle holder 24 moves toward a downward direction as shown FIG. 4a due to an elastic force of the spring 22. Then, the needle 25 mounted at the tip of the needle holder 24 is projected from the opening of the cylindrical member 26 and punctures the skin of the subject as shown in FIG. 4a. Upon puncture of the skin by the needle 25, body fluids leak out from the punctured skin.

After puncture, although the needle 25 tries to get back in the state as shown in FIG. 3 by a retention force of the spring 22, the needle 25 is fixed at the position of being opposed to the conductive membrane 27 as shown in FIG. 4b since the holder 24 is secured via the stopper 24a to a step 30.

The body fluids leaking from the skin penetrate throughout inside the cylindrical member 26 by sticking to the needle 25 or via the capillary phenomenon and are supplied to the electrode system. When the body fluids reach the reagent layer formed on the conductive membrane 27, the reagent layer dissolves in the body fluids and the enzyme in the reagent layer starts to mediate reaction.

As shown above, the present example uses the needle 25 not only as a puncture means of the skin of a subject but also as a working electrode of the sensor. This structure permits supply of a sample to the electrode system of the analysis element almost simultaneous with sampling. Moreover, this structure prevents drying of sample and decreases errors in measurement due to sample drying. Therefore, high accuracy measurement can be made with a trace amount of sample.

At measurement, since the stopper 24a of the needle holder 24 is secured to the step 29 after puncture, the amount of sample to be supplied to the cylindrical member 27 can be kept almost constant which results in decreased variations in the resultant response current.

EXAMPLE 2

The measurement device of Example 1 requires removal of the cap 23 before taking out the needle holder 24 in detaching the needle 25 although it allows easy detachment of the cylindrical member 27. This operation must be done at each measurement, rendering it much troublesome to make multiple measurements. In view of the above, an example of a measurement device which is similar to the measurement device of Example 1 but further comprises a needle attachment mechanism will be described in the present example.

Figure 5:
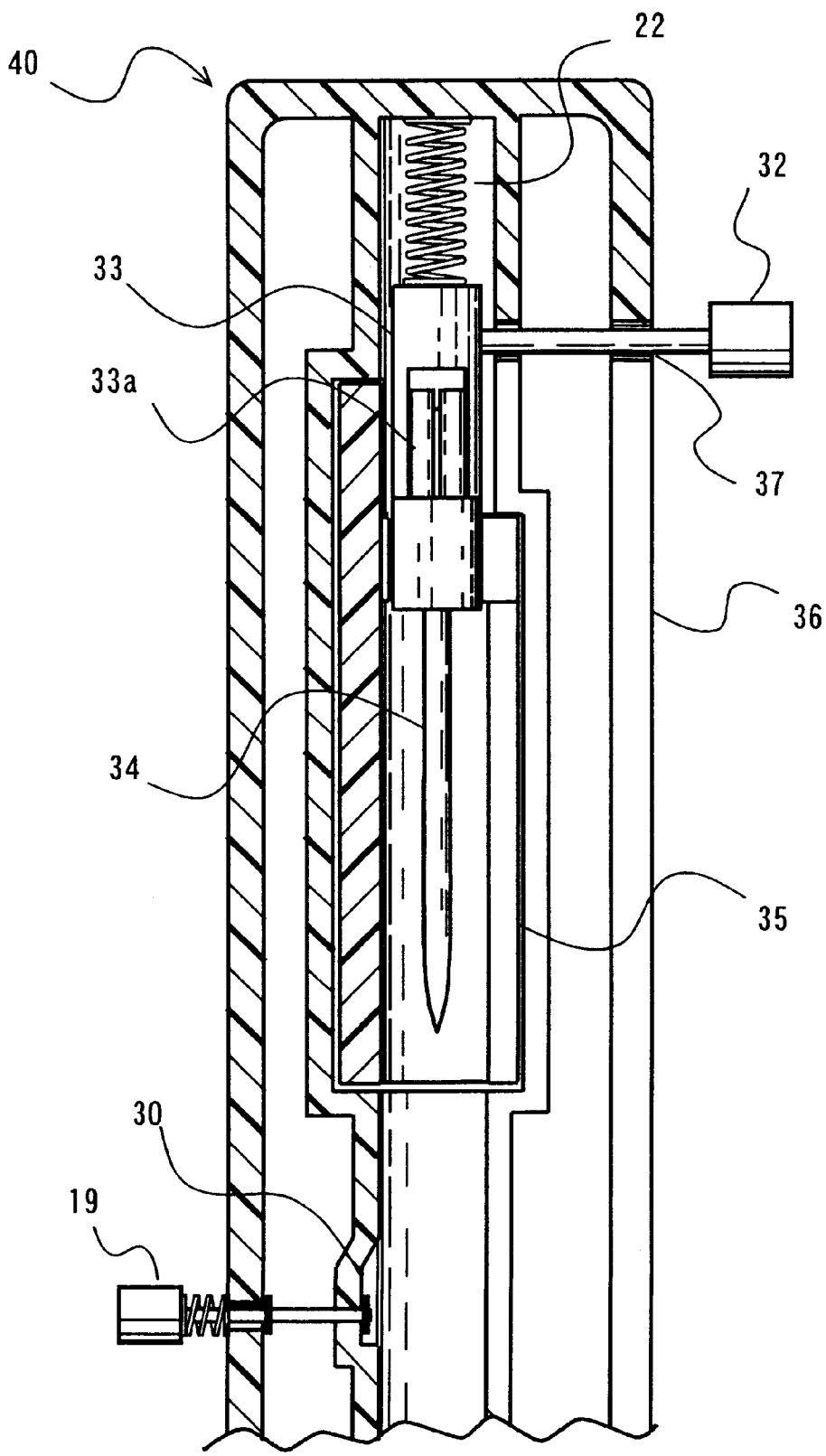
FIG. 5 is a longitudinal cross-sectional view illustrating essential parts of a measurement device of still other example of the present invention.
Figure 6:
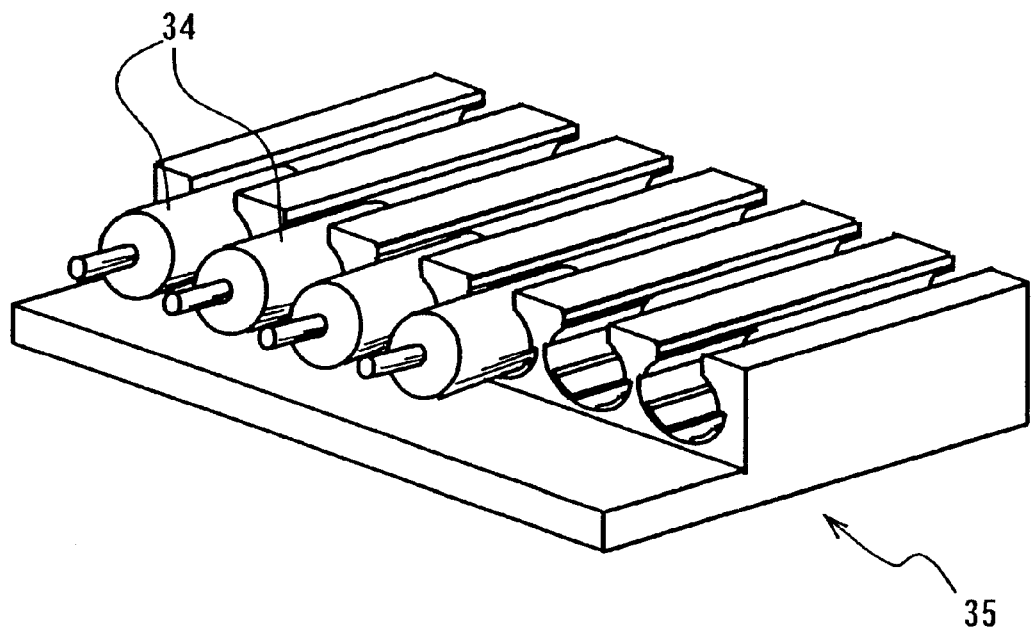
FIG. 6 is a perspective view of a cartridge used in the same measurement device.

Essential parts of the measurement device of this example are shown in FIG. 5. In the measurement device, a portion of the cylinder is cut out at the side proximal to the spring 22 from the switch 19 of the main body 40 in order to accommodate a cartridge 35 as shown in FIG. 6. The cartridge 35 has a plurality of cells each shaped approximately in correspondence with the shape of the inner wall of the cylinder. Each cell accommodates a needle 34 by securing it thereto.

A needle holder 33 is connected to a lever 32 for manually moving the needle holder 33 in the upward and downward direction of FIG. 5. The main body 40 is formed with a groove 36 for guiding the lever 32 on the side wall thereof. A hook 37 is disposed at an upper end of the groove 36 to secure the lever 32 at a position shown in FIG. 5. The needle 34 is detached in the following manner. At removal of the needle 34, an empty cell of the cartridge 35 is exposed to the cylinder. When the needle holder 33 secured at the step 29 or 30 is elevated up to the position shown in FIG. 5. the empty cell of the cartridge 35 accommodates the needle 34. Subsequent movement of the cartridge 35 in the vertical direction of the figure sheet releases a holder 33a and the needle 34 is released from the needle holder 33. Similar movement of the cartridge 35 to expose the cell accommodating a virgin needle 34 to the cylinder exchanges the used needle 34 with the virgin needle 34. Upon release of the lever 32 in this state, the needle holder 33 holding the new virgin needle 34 moves in the downward direction of FIG. 5 by an elastic force of the spring 22 and fixedly rested at the step 30.

A user can make measurement in the same manner as in Example 1 using the needle 34 mounted in the above-mentioned manner.

EXAMPLE 3

Measurement of the substrate concentration in body fluids by direct sampling of the body fluids from a subject as shown in the above two examples is likely to produce variations in the measured value depending on the amount of sample. In view of this, a measurement device facilitating accurate and precise measurement whether the amount of sample is large or small will be described in the present example.

One cause of the above-mentioned variations in the measured value is a difference in contact area between the sample and the working electrode. Regulation of contact area, therefore, is considered to enable more accurate and precise measurement.

In the present example, an electrically insulating film was coated on an identical needle to that of Example 1, excluding 1 mm proximal to the tip of the needle and 1 mm proximal to the root which is to be fixed to the needle holder 24.

Using a needle thus coated, blood glucose concentration was measured in the same manner as in Example 1. The result showed a current response dependent on the blood glucose concentration, which verified a drastic decrease in variations in the measured value, that is, current response.

As exemplified above, partial coating of the needle 25 doubling as the working electrode with an electrically insulating material regulates the area of the working electrode thereby enabling high accuracy measurement. Such coating also prevents short-circuiting between the needle 25 and the conductive membrane 27 located on the inner wall of the cylindrical member 26 thereby enabling stable measurement.

EXAMPLE 4

Variations in distance between the reagent layer and the working electrode at measurement due to movement of the needle electrode functioning as the working electrode impair measurement accuracy. An arrangement of the reagent layer on the conductive membrane 27 as was done in Example 1, for example, may vary the distance between the reagent layer and the working electrode when the position of the needle 25 is shifted from a predetermined position after puncture. This can produce a danger of errors in the measured value because conditions in the vicinity of an interface of the working electrode at sample supply (e.g., concentration of the electron acceptor in the vicinity of the working electrode, serial change in the concentration, etc.) may be changed from normal conditions.

An arrangement of the reagent layer on the needle 25 secures an almost equal environment in the vicinity of the interface of the working electrode at each measurement in the event of a shift of the position of a needle 16 from a predetermined position after puncture.

In the present example, the reagent layer was formed by applying a solution containing GOD and potassium ferricyanide onto a given position of the needle 25 and drying it. The needle thus produced was used to measure blood glucose concentration in the same manner as in Example 1. The result showed a current response dependent on the blood glucose concentration, which verified a decrease in variations in the measured value, that is, current response.

In the foregoing examples, although concrete examples of the analysis element and the measurement device in accordance with the present invention have been described, the present invention is not limited to those examples with respect to the shape and arrangement. A similar effect can be produced by a three-dimensional opposed arrangement of the membrane electrode formed on the inner wall of the cylindrical member and the needle member. For example, although the needle member was used as the working electrode and the membrane electrode as the counter electrode in the foregoing examples, this may be reversed. As the material for the working electrode, any material in addition to carbon can be used if it is conductive and would not be oxidized upon oxidation of the electron acceptor. As the material for the counter electrode, any conductive material of wide acceptance such as carbon, platinum, etc. can be used in addition to silver. The two electrodes may be formed from an electrically insulating material coated with one of those conductive materials. It is as a matter of course that the needle member should have a sufficient strength against puncture.

In the foregoing examples, although a voltage of 500 mV was applied onto the electrode system, the present invention is not limited to this value.

As the oxidoreductase, one fit for the quantitating substrate may be selected. Examples of the oxidoreductase are fructose dehydrogenase, glucose oxidase, alcohol oxidase, lactate oxidase, cholesterol oxidase, xanthine oxidase, amino acid oxidase, and so on.

Examples of the electron acceptor are potassium ferricyanide, p-benzoquinone, phenazine methosulfate, methylene blue, ferrocene derivatives and so on. The use of oxygen as the electron acceptor can also produce a current response. Those electron acceptors can be used singly or in combinations of two or more.

As an alternative, the reagent layer can be fixed on the working electrode to make the enzyme or the electron acceptor insoluble. Such fixation is preferably performed by cross-link fixation or adsorption.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for quantitating a substrate comprising the steps of:

preparing an analysis element comprising a needle electrode, a membrane electrode and a cylinder having a hollow space, said hollow space being open at least one end thereof, wherein said needle electrode is accommodated in said hollow space and said membrane electrode is formed on an inner wall of said hollow space;

pressing an opening of said cylinder against a subject to be examined;

projecting a tip of said needle electrode external to said opening of said cylinder temporarily to puncture said subject and collecting a sample from said subject;

introducing the collected sample between said membrane electrode and said needle electrode in said cylinder;

reacting a substrate contained in said sample with an oxidoreductase; and applying a voltage across said membrane electrode and said needle electrode and measuring resultant current in said membrane electrode or said needle electrode.

2. A measurement device for electrochemically quantitating a concentration of a substrate contained in a sample based on reaction between said substrate and an oxidoreductase, said device comprising:

an element having a cylindrical hollow space, said space being open at least one end thereof;

a membrane electrode formed on an inner wall of said hollow space;

a needle electrode accommodated in said hollow space; and means for projecting a tip of said needle electrode external to said hollow space temporarily.

3. The measurement device in accordance with claim 2, wherein said needle member is formed with an electrically insulating layer on a portion of the surface thereof.

4. The measurement device in accordance with claim 2, wherein said needle member is formed with a reagent layer containing an electron acceptor and an oxi-doreductase on the surface thereof.

5. The measurement device in accordance with claim 2, wherein said hollow space is further formed with a reagent layer containing an electron acceptor and an oxidoreductase on an inner wall thereof.

6. The measurement device in accordance with claim 2 further comprising a unit for fixing the needle electrode at the predetermined position after the projection of said needle electrode.

* * * * *